United States Patent
Atanasiu

(10) Patent No.: US 10,360,218 B2
(45) Date of Patent: Jul. 23, 2019

(54) SYSTEM AND METHODS FOR CACHING AND QUERYING OBJECTS STORED IN MULTIPLE DATABASES

(71) Applicant: HYLAND SWITZERLAND SÀRL, Geneva (CH)

(72) Inventor: Razvan Atanasiu, Victoria, MN (US)

(73) Assignee: HYLAND SWITZERLAND SÀRL, Geneva (CH)

(*) Notice: Subject to any disclaimer, the term of this patent is extended or adjusted under 35 U.S.C. 154(b) by 381 days.

(21) Appl. No.: 14/502,895

(22) Filed: Sep. 30, 2014

(65) Prior Publication Data

US 2015/0095364 A1    Apr. 2, 2015

Related U.S. Application Data

(60) Provisional application No. 61/884,961, filed on Sep. 30, 2013.

(51) Int. Cl.
| | | |
|---|---|---|
| G06F 17/30 | (2006.01) | |
| G06F 16/2455 | (2019.01) | |
| G06F 16/2458 | (2019.01) | |
| G06F 19/00 | (2018.01) | |

(52) U.S. Cl.
CPC .... G06F 16/24552 (2019.01); G06F 16/2471 (2019.01); G06F 19/321 (2013.01)

(58) Field of Classification Search
CPC ........... G06F 17/3048; G06F 17/30545; G06F 17/30445
USPC ........................................................ 707/764
See application file for complete search history.

(56) References Cited

U.S. PATENT DOCUMENTS

| | | | | |
|---|---|---|---|---|
| 6,014,671 | A * | 1/2000 | Castelli | G06F 16/51 |
| 2009/0164247 | A1* | 6/2009 | Dobler | G06F 19/321 |
| | | | | 705/3 |
| 2010/0138446 | A1* | 6/2010 | Canessa | G06F 15/16 |
| | | | | 707/770 |
| 2010/0235323 | A1* | 9/2010 | Zhang | G06F 19/321 |
| | | | | 707/623 |
| 2011/0213774 | A1* | 9/2011 | Buurman | G16H 10/60 |
| | | | | 707/736 |

(Continued)

OTHER PUBLICATIONS

Oracle, "Oracle7 Tuning, release 7.3.3: Parallel Query Concepts", Mar. 1, 2012, <https://web.archive.org/web/20120301121235/http://docs.oracle.com/cd/A57673_01/DOC/server/doc/A48506/pqoconce.htm>.*

(Continued)

Primary Examiner — Hosain T Alam
Assistant Examiner — Robert F May
(74) Attorney, Agent, or Firm — Medley, Behrens & Lewis, LLC

(57) ABSTRACT

A method for organizing and searching objects from a plurality of databases includes querying an attribute of each entry stored in the plurality of databases; assigning a memory value for each of the attributes retrieved from each of the objects stored in the plurality of databases and storing the memory values for each of the attributes in a cache. At a client device, a search query is received and it is determined if the search query contains an attribute of the entry to be searched. Upon positive determination, a search is performed at the cache using the attribute contained in the search query; and upon negative determination, a search for the entry is performed at the plurality of databases.

3 Claims, 3 Drawing Sheets

(56) References Cited

U.S. PATENT DOCUMENTS

| | | | |
|---|---|---|---|
| 2011/0225266 A1* | 9/2011 | Douglas | G06F 19/321 709/219 |
| 2012/0303896 A1* | 11/2012 | McGroddy-Goetz | G06F 12/0866 711/118 |
| 2014/0379837 A1* | 12/2014 | Gasser | H04L 67/2847 709/213 |
| 2015/0006574 A1* | 1/2015 | Saalbach | G06F 19/321 707/772 |

OTHER PUBLICATIONS

Roni Zaharia, "DICOM is Easy", Dec. 1, 2011, Blogger <http://dicomiseasy.blogspot.com/2011/12/chapter-4-dicom-objects-in-chapter-3.html>.*

Roni Zaharia, "DICOM is Easy", Dec. 1, 2011, Blogger <http://dicomiseasy.blogspot.com/2011/12/chapter-4-dicom-objects-in-chapter-3.html> (Year: 2011).*

* cited by examiner

SYSTEM AND METHODS FOR CACHING AND QUERYING OBJECTS STORED IN MULTIPLE DATABASES

CROSS REFERENCES TO RELATED APPLICATIONS

Pursuant to 35 U.S.C. § 119, this application claims the benefit of the earlier filing date of Provisional Application Ser. No. 61/884,961, filed Sep. 30, 2013, entitled "System and Methods for Caching Objects Stored in Multiple Databases," the content of which is hereby incorporated by reference herein in its entirety.

STATEMENT REGARDING FEDERALLY SPONSORED RESEARCH OR DEVELOPMENT

None.

REFERENCE TO SEQUENTIAL LISTING, ETC.

None.

BACKGROUND

1. Technical Field

The present disclosure relates generally to systems and methods for caching and querying objects in multiple databases and more particularly, caching and querying Digital Imaging and Communications in Medicine (DICOM) objects.

2. Description of the Related Art

For an application that uses multiple databases, caching is one of the most important factors that could improve performance. Caching stores data into a memory in a way that future requests for those data may be served faster. However, with multiple databases that contain hundreds or thousands of entries, caching and the subsequent retrieval of entries may take a considerable amount of time.

Typically, searching for an object from a plurality of databases is performed using parallel query. Parallel query allows a system to break up a given query so that its parts can run simultaneously on different processors to search for an object from a plurality of databases. Parallel query can improve performance on a multiple-database system but it still has drawbacks such as a longer processing time and scalability problems during higher concurrency situations.

Accordingly, there is a need for a method of caching and querying for objects stored in a database faster and more efficiently. There is a need for a method that can be used to search for objects prior to resorting to parallel query.

SUMMARY

A method for caching objects stored in a plurality of databases is disclosed. The method includes querying the plurality of databases, creating a memory structure based on the database entries, and assigning a memory value for a particular level in the databases. The memory value is used to search for an object when a query for a DICOM object is received from a client.

In another aspect of the present disclosure, a method for organizing and searching objects from a plurality of databases is disclosed. The method includes retrieving, by a server, entries from the plurality of databases by querying an attribute of each entry stored in the plurality of databases. The method further includes assigning, by the server, a memory value for each of the attributes retrieved from each of the entries stored in the plurality of databases.

The memory values may be stored for each of the attributes in a cache and at a client device, a search query may be received. The search query may be a query for a first entry stored in one of the plurality of databases. At the client device, a determining may be performed if the search query contains an attribute of the first entry to be searched. Upon positive determination, performing a search at the cache using the attribute contained in the search query; and upon negative determination, performing a search for the first entry at the plurality of databases.

From the foregoing disclosure and the following detailed description of various example embodiments, it will be apparent to those skilled in the art that the present disclosure provides a significant advance in the art of methods for enabling network-based processes in a device during a network downtime condition. Additional features and advantages of various example embodiments will be better understood in view of the detailed description provided below.

BRIEF DESCRIPTION OF THE DRAWINGS

The above-mentioned and other features and advantages of the present disclosure, and the manner of attaining them, will become more apparent and will be better understood by reference to the following description of example embodiments taken in conjunction with the accompanying drawings. Like reference numerals are used to indicate the same element throughout the specification.

DETAILED DESCRIPTION OF THE DRAWINGS

Figure 1:
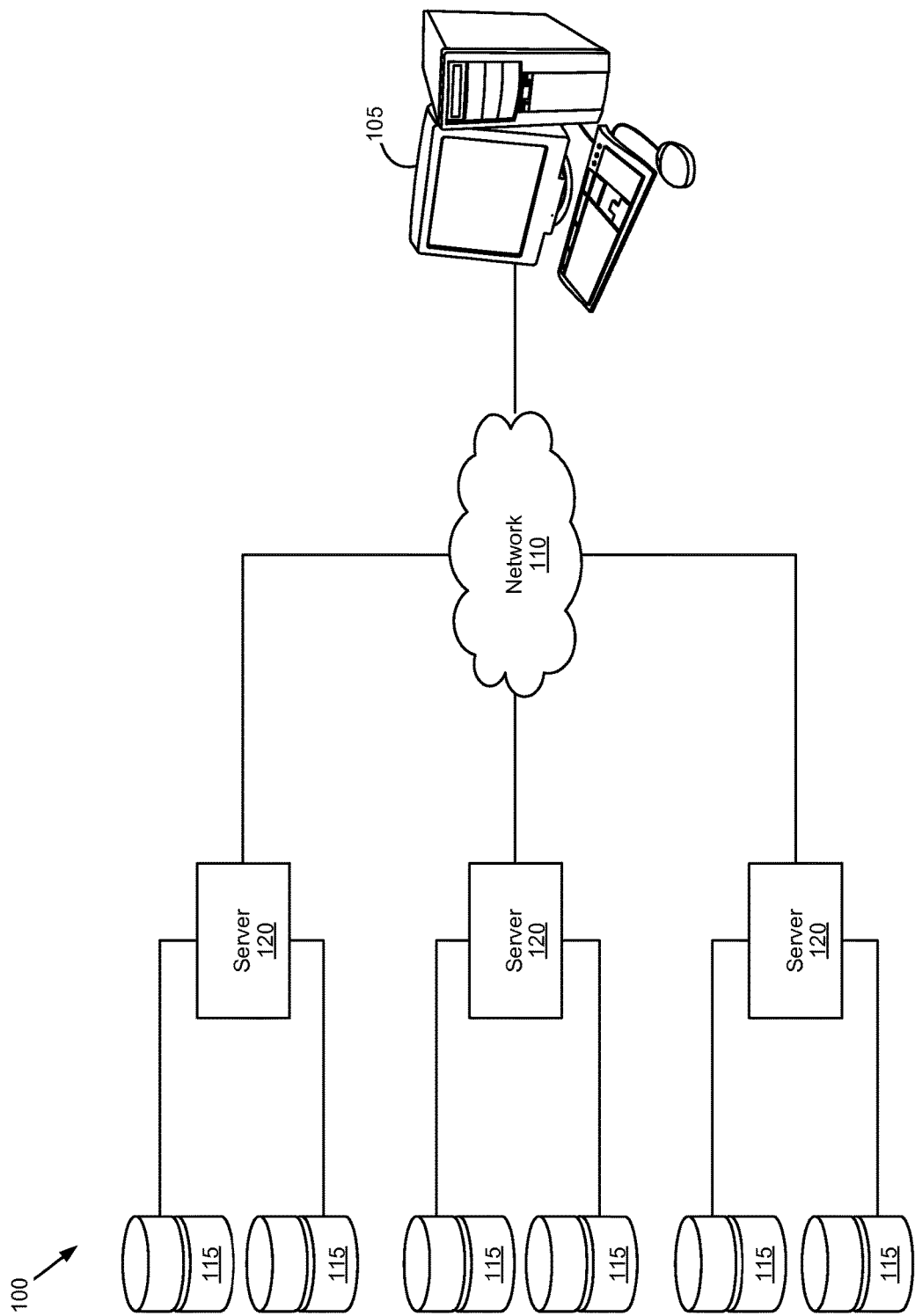
FIG. 1 is an example system for accessing DICOM objects using a client device from one or more remote databases connected through a network.

It is to be understood that the disclosure is not limited to the details of construction and the arrangement of components set forth in the following description or illustrated in the drawings. The disclosure is capable of other example embodiments and of being practiced or of being carried out in various ways. For example, other example embodiments may incorporate structural, chronological, process, and other changes. Examples merely typify possible variations. Individual components and functions are optional unless explicitly required, and the sequence of operations may vary. Portions and features of some example embodiments may be included in or substituted for those of others. The scope of the disclosure encompasses the appended claims and all available equivalents. The following description is, therefore, not to be taken in a limited sense, and the scope of the present disclosure is defined by the appended claims.

Also, it is to be understood that the phraseology and terminology used herein is for the purpose of description and should not be regarded as limiting. The use herein of "including," "comprising," or "having" and variations thereof is meant to encompass the items listed thereafter and equivalents thereof as well as additional items. Further, the use of the terms "a" and "an" herein do not denote a limitation of quantity but rather denote the presence of at least one of the referenced item.

In addition, it should be understood that example embodiments of the disclosure include both hardware and electronic components or modules that, for purposes of discussion, may be illustrated and described as if the majority of the components were implemented solely in hardware.

It will be further understood that each block of the diagrams, and combinations of blocks in the diagrams, respectively, may be implemented by computer program instructions. These computer program instructions may be loaded onto a general purpose computer, special purpose computer, or other programmable data processing apparatus to produce a machine, such that the instructions which execute on the computer or other programmable data processing apparatus may create means for implementing the functionality of each block or combinations of blocks in the diagrams discussed in detail in the description below.

These computer program instructions may also be stored in a non-transitory computer-readable medium that may direct a computer or other programmable data processing apparatus to function in a particular manner, such that the instructions stored in the computer-readable medium may produce an article of manufacture, including an instruction means that implements the function specified in the block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus implement the functions specified in the block or blocks.

Accordingly, blocks of the diagrams support combinations of means for performing the specified functions, combinations of steps for performing the specified functions and program instruction means for performing the specified functions. It will also be understood that each block of the diagrams, and combinations of blocks in the diagrams, can be implemented by special purpose hardware-based computer systems that perform the specified functions or steps, or combinations of special purpose hardware and computer instructions.

Disclosed are a system and methods for caching entries in a database. A method is disclosed that queries a plurality of databases, creates a memory structure based on the entries on the database, and assigns a memory value for each entry of a particular level in the database. The level is associated to an object that is retrieved from a database by referencing the memory structure, as will be discussed in greater detail herein.

For purposes of the present disclosure, it will be appreciated that the object may refer to files such as, for example, documents, image files, audio files, among others. Object may refer to paper-based records converted into digital files to be used by a computing device. Object may also refer to information that provides value for an end-user or object consumer in one or more specific contexts. Object may be shared via one or more media such as, for example, computing devices in a network.

In an example embodiment, object may refer to computerized medical records, or electronic medical records (EMR), created in a health organization, or any organization that delivers patient care such as, for example, a physician's office, a hospital, or ambulatory environments. EMR may include orders for drug prescriptions, orders for tests, patient admission information, imaging test results, laboratory results, and clinical progress information, among others.

Object may also refer to an electronic health record (EHR) which may be a digital object capable of being distributed, accessed or managed across various health care settings. EHRs may include various types of information such as, for example, medical history, demographics, immunization status, radiology images, medical allergies, personal states (e.g. age, weight), vital signs and billing information, among others. EHR and EMR may also be referred to as electronic patient record (EPR). The terms EHR, EPR, EMR, document, object, object and assets may be used interchangeably for illustrative purposes throughout the present disclosure.

In another example embodiment, object may also refer to DICOM objects. DICOM is a standard or specification for transmitting, storing, printing and handling information in medical imaging. Medical imaging, as will be known in the art, may refer to a process and/or technique used to generate images of the human body, or parts or functions thereof, for medical and/or clinical purposes such as, for example, to diagnose, reveal or examine a disease. The standard set by DICOM may facilitate interoperability of various medical imaging equipment across a domain of health enterprises by specifying and/or defining data structures, workflow, data dictionary, compression and workflow, among other things, for use to generate, transmit and access the images and related information stored on the images. DICOM object may refer to medical images following the file format definition and network transmission protocol as defined by DICOM. DICOM object may include a range of biological imaging results and may include images generated through radiology and other radiological sciences, nuclear medicine, thermography, microscopy, microscopy and medical photography, among many others. DICOM object may be referred to hereinafter as images following the DICOM standard, and non-DICOM object for other forms and types of object, as will be known in the art.

The DICOM object may be generated and maintained within an institution such as, for example, an integrated delivery network, hospital, physician's office or clinic, to provide patients and health care providers, insurers or payers access to records of a patient across a number of facilities. Sharing of an object may be performed using network-connected enterprise-wide information systems, and other similar information exchanges or networks, as will be known in the art.

FIG. 1 shows an example system for accessing DICOM objects using a client device and one or more remote databases connected through a network. The system includes an example client 105, a network 110, a plurality of databases 115, and a server 220.

Client 105 may be a computing device that allows a user to search and access DICOM objects from the plurality of databases 115. Client 105 may be used by a user of a web page or a web application (not shown) to request for a DICOM object by submitting a query for the DICOM object and receiving one or more results corresponding to the query. In an example embodiment, client 105 may be a medical information system that is used by one or more users to retrieve DICOM objects, as will be known.

Network 110 may be any network, communications network or network/communications network system such as, but not limited to, a peer-to-peer network, a hybrid peer-to-peer network, a Local Area Network (LAN), a Wide Area Network (WAN), a public network, such as the Internet, a private network, a cellular network, a combination of different network types, or other wireless, wired, and/or a wireless and wired combination network capable of allowing communication between two or more computing systems, as discussed herein, and/or available or known at the time of filing, and/or as developed after the time of filing.

Metadata associated with the DICOM objects may be stored in databases 115. Databases 115 may be Medical Object Manager (MCM) or a picture archiving and communication system (PACS) systems. DICOM metadata may be stored in databases 115 for specified periods of time. When client 105 requests for a DICOM object, it connects to at least one of the databases 115 through network 110 and fetches the stored metadata associated with the object to locate and retrieve the object. To connect to databases, client 105 must be familiar with the specific protocol for communicating with the database.

Server 220 may be a Web Access to DICOM Persistent Objects (WADO) server that connects the client with databases 115 using network 110. The WADO server 220 simplifies the communication between client 105 and any DICOM database by providing protocols and mechanisms for accessing DICOM objects through HTTP/HTTPS, and using a DICOM Unique Identifier (UID). With WADO, any web client is able to query for DICOM objects such as, medical images, reports and other object formats, from the databases 115.

Figure 2:
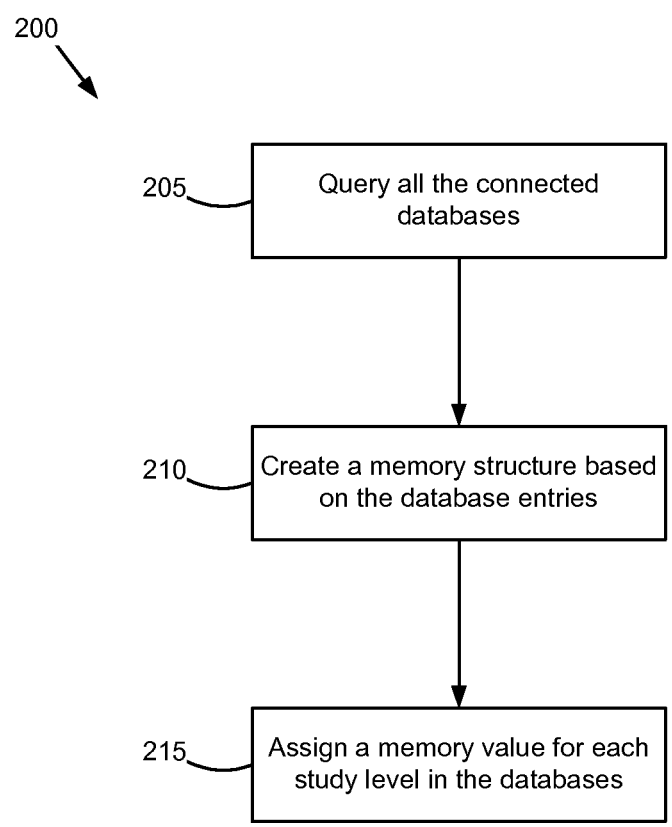
FIG. 2 is an example method of caching DICOM objects.

FIG. 2 shows an example method 200 of caching DICOM objects such that a query for a DICOM object may be made faster and more efficient. In FIG. 1, which illustrates an example system having a plurality of databases 115, a DICOM query is typically performed using a parallel query on the plurality of databases to retrieve a DICOM object from databases 115. Example method 200 caches the objects beforehand in order to allow a DICOM query to check the cache first to easily locate an object, before going the more typical route of parallel querying.

Method 200 may be performed by a web service in client 105 when querying and retrieving objects through network 110 to and from at least one database of databases 115. The web service may be configured to expose a web service endpoint and a RESTful endpoint. Method 200 may be performed with WADO requests. WADO requests are performed at the DICOM instance level, wherein each request requires three key values: StudyInstanceUID, SeriesInstanceUID and SOPInstanceUID.

At block 205, all of the databases 115 that are connected to client 105 are queried and a cache memory structure based on the database entries is created (at block 210) by assigning a memory value for each entry having a level in the databases (at block 215). Creating the memory structure and assigning a memory value for each database entry of a specific level such as, for example, the StudyInstanceUID, in databases 115 aggregates the plurality of databases and allows client 105 to run one query on the cache to find a DICOM object, before resorting to the slower process of parallel query. Using method 200 that caches the StudyInstanceUID and DICOM database pairs uses a single service or process that would serve all application servers 120, therefore making the system more scalable.

In an example embodiment, other items may also be cached such as the Study GUIDs. In an alternative example embodiment, a timestamp of the run time of caching the entries may be kept and a dynamic query may be performed to check which entries are recently added. If a StudyInstanceUID value is found in more than one database, either the last entry visited is cached or all entries found are being stored in a list.

Polling operations that cache new entries may be performed similarly by querying the database for new entries and adding the new entries in the memory structure by assigning a corresponding memory value for each new entry. In an alternative example embodiment, options for caching the entries may be configured. Configurable options include the databases that may be queried for storing entries in the cache and the polling intervals (e.g., 5 minutes, 10 minutes, etc.).

Figure 3:
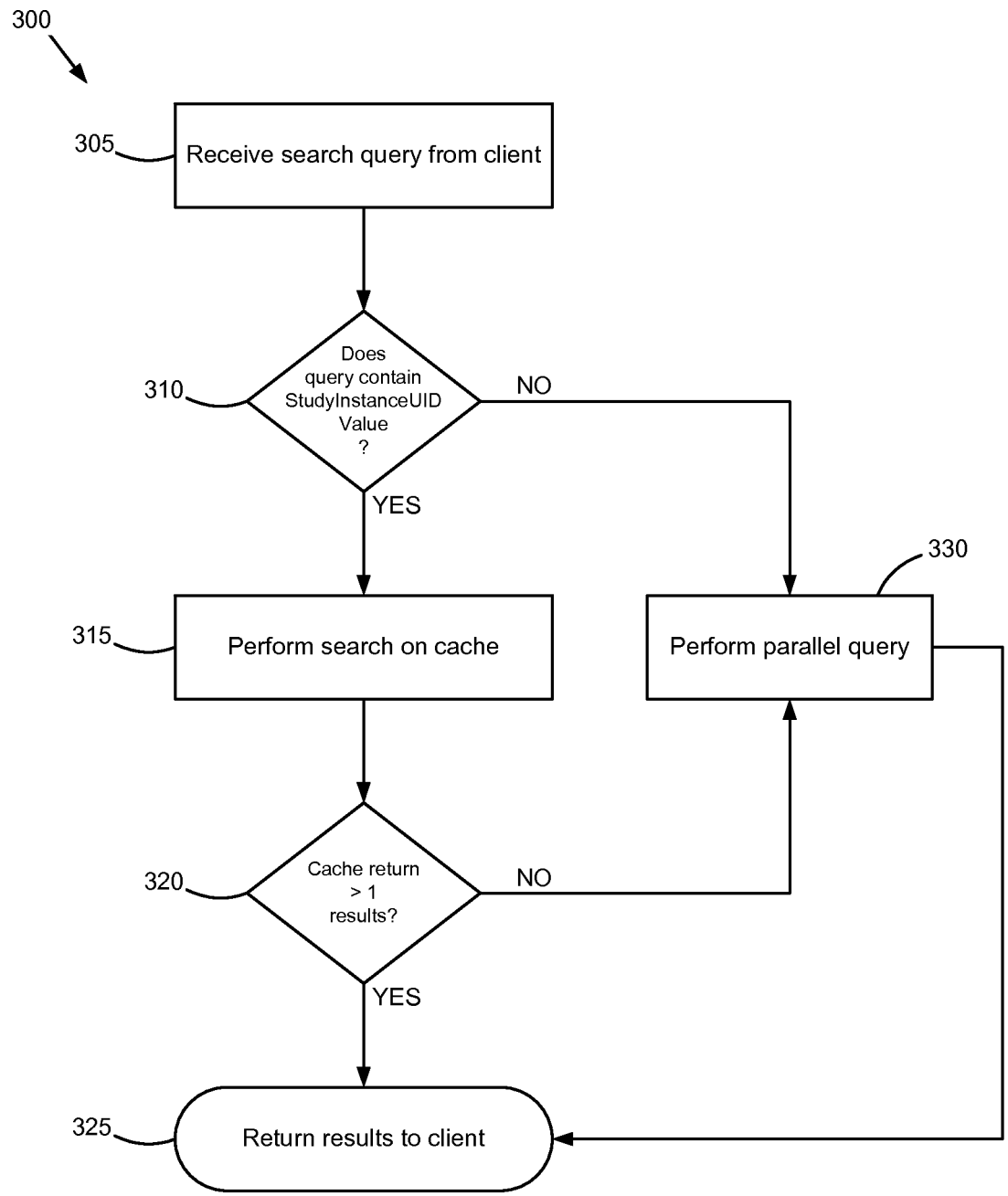
FIG. 3 is an example method of performing a query and retrieve DICOM operation.

FIG. 3 is an example method 300 of performing a query and retrieve DICOM operation. Method 300 may also be performed with WADO requests. As aforementioned, WADO requests are performed at the DICOM instance level, wherein each request requires three key values: StudyInstanceUID, SeriesInstanceUID and SOPInstanceUID.

At block 305, a search query may be received from client 105. The search query may be a Query/Retrieve (QR) DICOM query that contains a search term that users of client 105 wishes to access a DICOM object with. If the search query received is a WADO query, StudyInstanceUID is guaranteed to be part of the request and is then used to perform search on cache at block 315. However, for other DICOM queries, the received Q/R dataset may be first determined if it contains a StudyInstanceUID value (at block 310). If the received dataset contains a StudyInstance UID value, a search is performed on the cache to determine if a StudyInstanceUID and a DICOM object is present on the cache that will allow the system to identify the database associated with the StudyInstanceUID (at block 315), thereby performing only one query.

At block 320, if the cache returns a positive result (i.e., a result greater than one) which indicates that a StudyInstanceUID associated with the query is found on the cache, the DICOM object associated with the StudyInstanceUID is then retrieved from the database that is specified in the cache. The retrieved DICOM object is then returned to client 105 (at block 325).

However, if at block 320, it is determined that the StudyInstanceUID has not been previously cached, and the cache returns a negative value, the more traditional method of locating DICOM objects through parallel query may be performed (at block 330).

In continued reference to block 310, if the query does not contain a to StudyInstanceUID value, a parallel query may be performed on the databases to retrieve the DICOM object associated with the query (at block 330), and the results returned to client 105 (at block 325).

It will be understood that the example applications described herein are illustrative and should not be considered limiting. It will be appreciated that the actions described and shown in the example flowcharts may be carried out or performed in any suitable order. It will also be appreciated that not all of the actions described in FIGS. 2 and 3 need to be performed in accordance with the example embodiments of the disclosure and/or additional actions may be performed in accordance with other example embodiments of the disclosure.

Many modifications and other example embodiments of the disclosure set forth herein will come to mind to one skilled in the art to which these disclosure pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for organizing and searching objects from a plurality of databases, comprising:

a plurality of databases storing one or more objects, each object having at least one attribute comprising a SOPInstanceUID;
a computing device connected to the plurality of databases, the computing device having one or more instructions for:
retrieving at least one attribute for each of the one or more objects stored in the plurality of databases;
assigning a memory value for each retrieved attribute of the one or more objects;
storing the memory values in a cache; and
updating the cache by querying each of the plurality of databases for newly-added objects and assigning a corresponding memory value for each of the newly-added objects; and
a client imaging device connected to the plurality of databases for:
receiving a search query for a first object;
determining if the search query includes an attribute value for searching the first object;
upon positive determination that the search query includes the attribute value for searching the first object, perform a search for the first object on the cache using the attribute value contained in the search query; and
upon negative determination that the search query does not include the attribute value, perform a search for the first object on the plurality of databases;
wherein the newly-added objects in the plurality of databases have not been previously retrieved; and
wherein the newly-added objects in the plurality of databases do not have a corresponding memory value assigned prior to the querying;
wherein each of the newly-added objects from the plurality of databases is a DICOM database object;
wherein the attribute of each of the DICOM database objects is a DICOM level attribute;
wherein the querying is repeated according to a pre-defined polling interval;
wherein the search query is a Web Access to DICOM Persistent Objects (WADO) request;
wherein the search query is performed as a parallel query;
wherein the attribute of the first object to be searched comprises:
a StudyInstanceUID corresponding to the first object; and
a timestamp corresponding to a runtime of caching the first object;
wherein retrieving the at least one attribute for each of the one or more objects stored in the plurality of databases further comprises determining a most recently added one of the objects sharing the attribute and stored in the plurality of databases;
wherein the assigning the memory value for each of the attributes further includes pairing each of the attribute with the corresponding object in the plurality of databases;
wherein the pairing each of the attribute with the corresponding object in the plurality of the databases includes pairing each of the attribute with a storage location of the corresponding object;
wherein if performing the search at the cache using the attribute contained in the search query returns at least one attribute from the cache, retrieving the object using the storage location paired with the attribute;
wherein each attribute is associated with one of a plurality of specific levels within one or more of the plurality of databases;
wherein each attribute further comprises:
a unique StudyInstanceID corresponding to some or all of the objects stored in the plurality of databases;
a SeriesinstanceUID;
a SOPInstanceUID;
a unique identifier corresponding to one or more of the objects stored in the plurality of databases; and
a timestamp of a runtime of caching one or more of the objects stored in the plurality of databases.

2. A method for organizing and searching objects from a plurality of databases, comprising:
retrieving, by a server, entries from the plurality of databases by querying at least one attribute of each entry stored in the plurality of databases;
assigning, by the server, a memory value for each of the attributes retrieved from each of the entries stored in the plurality of databases;
storing the memory values for each of the attributes in a cache;
receiving at a client device a search query for a first entry stored in one of the plurality of databases;
determining at the client device if the search query contains an attribute of the first entry to be searched;
upon positive determination, performing a search at the cache using the attribute contained in the search query;
upon negative determination, performing a search for the first entry at the plurality of databases;
updating the cache by querying each of the plurality of databases for newly-added entries and assigning a corresponding memory value for each of the newly-added entries;
wherein the newly-added entries in the plurality of databases have not been previously retrieved; and
wherein the newly-added entries in the plurality of databases do not have a corresponding memory value assigned prior to the querying;
wherein each of the newly-added entries from the plurality of databases is a DICOM database entry;
wherein the attribute of each of the DICOM database entries is a DICOM level attribute;
wherein the querying is repeated according to a pre-defined polling interval;
wherein the search query is a Web Access to DICOM Persistent Objects (WADO) request;
wherein the search query is performed as a parallel query;
wherein the attribute of the first entry to be searched comprises:
a StudyInstanceUID corresponding to the first entry; and
a timestamp corresponding to a runtime of caching the first entry;
wherein querying the attribute of each entry stored in the plurality of databases further comprises determining a most recently added one of the entries sharing the attribute and stored in the plurality of databases
wherein the assigning the memory value for each of the attributes further includes pairing each of the attribute with the corresponding entry in the plurality of databases;
wherein the pairing each of the attribute with the corresponding entry in the plurality of the databases includes pairing each of the attribute with a storage location of the corresponding entry;

wherein if the performing the search at the cache using the attribute contained in the search query returns at least one attribute from the cache, the method further includes retrieving the entry using the storage location paired with the attribute;

wherein each attribute is associated with one of a plurality of specific levels within one or more of the plurality of databases;

wherein each attribute comprises:
- a unique StudyInstanceID corresponding to some or all of the entries stored in the plurality of databases;
- a SeriesinstanceUID;
- a SOPInstanceUID;
- a unique identifier corresponding to one or more of the entries stored in the plurality of databases; and
- a timestamp of a runtime of caching one or more of the entries stored in the plurality of databases.

3. A computer program product comprising a non-transitory computer readable medium having computer program instructions stored thereon, the computer program instructions configured to cause a server, upon execution thereof, to perform a method for organizing and searching objects from a plurality of databases, the method comprising:

retrieving, by a server, entries from the plurality of databases by querying at least one attribute of each entry stored in the plurality of databases;

assigning, by the server, a memory value for each of the attributes retrieved from each of the entries stored in the plurality of databases;

storing the memory values for each of the attributes in a cache;

receiving at a client device a search query for a first entry stored in one of the plurality of databases;

determining at the client device if the search query contains an attribute of the first entry to be searched;

upon positive determination, performing a search at the cache using the attribute contained in the search query;

upon negative determination, performing a search for the first entry at the plurality of databases;

updating the cache by querying each of the plurality of databases for newly-added entries and assigning a corresponding memory value for each of the newly-added entries;

wherein the newly-added entries in the plurality of databases have not been previously retrieved; and wherein the newly-added entries in the plurality of databases do not have a corresponding memory value assigned prior to the querying;

wherein each of the newly-added entries from the plurality of databases is a DICOM database entry;

wherein the attribute of each of the DICOM database entries is a DICOM level attribute;

wherein the querying is repeated according to a predefined polling interval;

wherein the search query is a Web Access to DICOM Persistent Objects (WADO) request;

wherein the search query is performed as a parallel query;

wherein the attribute of the first entry to be searched comprises:
- a StudyInstanceUID corresponding to the first entry; and
- a timestamp corresponding to a runtime of caching the first entry;

wherein querying the attribute of each entry stored in the plurality of databases further comprises determining a most recently added one of the entries sharing the attribute and stored in the plurality of databases wherein the assigning the memory value for each of the attributes further includes pairing each of the attribute with the corresponding entry in the plurality of databases;

wherein the pairing each of the attribute with the corresponding entry in the plurality of the databases includes pairing each of the attribute with a storage location of the corresponding entry;

wherein if the performing the search at the cache using the attribute contained in the search query returns at least one attribute from the cache, the method further includes retrieving the entry using the storage location paired with the attribute;

wherein each attribute is associated with one of a plurality of specific levels within one or more of the plurality of databases;

wherein each attribute further comprises:
- a unique StudyInstanceID corresponding to some or all of the entries stored in the plurality of databases;
- a SeriesinstanceUID;
- a SOPInstanceUID;
- a unique identifier corresponding to one or more of the entries stored in the plurality of databases; and
- a timestamp of a runtime of caching one or more of the entries stored in the plurality of databases.

* * * * *